United States Patent
de Lazaro Casagrande Junior et al.

(10) Patent No.: US 8,993,775 B2
(45) Date of Patent: Mar. 31, 2015

(54) CHROMIUM AND NICKEL CATALYSTS FOR OLIGOMERIZATION REACTIONS AND PROCESS FOR OBTAINING ALPHA-OLEFINS USING SAID CATALYSTS

(75) Inventors: Osvaldo de Lazaro Casagrande Junior, Porto Alegre (BR); Carlos Rene Klotz Rabello, Rio de Janeiro (BR); Lucilene Losch de Oliveira, Porto Alegre (BR); Ana Helena Dias Pereira dos Santos, Porto Alegre (BR); Roberta Campedelli, Porto Alegre (BR); Adao Lauro Bergamo, Porto Alegre (BR)

(73) Assignees: Petroleo Brasileiro S.A.—Petrobras, Rio de Janeiro (BR); Universidade Federal do Rio Grande do Sul-UFRGS, Rio de Janeiro (BR)

( * ) Notice: Subject to any disclaimer, the term of this patent is extended or adjusted under 35 U.S.C. 154(b) by 140 days.

(21) Appl. No.: 13/250,439

(22) Filed: Sep. 30, 2011

(65) Prior Publication Data

US 2012/0178939 A1 Jul. 12, 2012

(51) Int. Cl.
*C07F 15/04* (2006.01)
*C07C 2/02* (2006.01)
*C07C 2/32* (2006.01)
*C07F 11/00* (2006.01)

(52) U.S. Cl.
CPC ............... *C07F 15/045* (2013.01); *C07C 2/32* (2013.01); *C07F 11/005* (2013.01); *C07C 2531/14* (2013.01); *C07C 2531/22* (2013.01)
USPC ............................ 548/101; 585/520; 585/525

(58) Field of Classification Search
USPC .................................. 548/101; 585/520, 525
See application file for complete search history.

(56) References Cited

FOREIGN PATENT DOCUMENTS

JP 2001187345 A * 7/2001 ............... B01J 31/20

OTHER PUBLICATIONS

Yoshida et al. CAS Accession No. 2001:495248.*
English Translation of JP 2001-187345, accessed Nov. 17, 2013.*
Oliveira et al. "Highly selective nickel catalysts for ethylene oligomerization based on tridentate pyrazolyl ligands" Journal of Molecular Catalysis A: Chemical, 2008, vol. 288, pp. 58-62.*
Mahapatra et al. CAS Accession No. 1993:461608.*
Ojwach et al. "(Pyrazol-1-ylmethyl)pyridine Nickel Complexes: Ethylene Oligomerization and Unusual Friedel—Crafts Alkylation Catalysts" Organometallics, 2009, vol. 28, pp. 2127-2133.*
Hurtado et al. "Chromium(III) complexes with terdentate 2,6-bis(azolylmethyl)pyridine ligands: Synthesis, structures and ethylene polymerization behavior" Journal of Organometallic Chemistry, 2009, vol. 694, pp. 2636-2641.*

* cited by examiner

*Primary Examiner* — Joseph Kosack
(74) *Attorney, Agent, or Firm* — Sughrue Mion, PLLC

(57) ABSTRACT

The present invention refers to the synthesis of precatalysts and the use of such precatalysts in ethylene oligomerization reactions for the selective production of alpha-olefins. More specifically, it refers to the preparation and use of coordination compounds containing polydentate ligands comprising Group 6 and 10 transition metal compounds, in particular chromium (III) and nickel (II). Such catalytic precursors present high catalytic activity and selectivity for the production of alpha-olefins.

21 Claims, No Drawings

CHROMIUM AND NICKEL CATALYSTS FOR OLIGOMERIZATION REACTIONS AND PROCESS FOR OBTAINING ALPHA-OLEFINS USING SAID CATALYSTS

FIELD OF INVENTION

The present invention refers to the synthesis of precatalysts and the use of such precatalysts in ethylene oligomerization reactions to selectively produce alpha-olefins. More specifically, the present invention refers to the synthesis of polydentate Periodic Table Group 6 and 10 transition metal coordination compounds, and using such compounds as olefin oligomerization catalysts, specifically in ethylene dimerization and trimerization, for the selective production of alpha-olefins.

BASIS OF THE INVENTION

The alpha-olefins that are of greater interest to industry are linear hydrocarbons containing from 4 to 20 carbon atoms. In oligomerization, carbon chains are linked through the end of the chains in the alpha position via double bonds. Oligomers are used not only to produce surfactants and synthetic lubricant materials, but also as co-monomers to produce olefin polymers (polyolefins). In recent decades, more active and more selective catalytic systems have been developed, enabling cheaper processes to oligomerize and/or trimerize olefins.

In the state of the art we often find catalytic ethylene oligomerization systems to produce higher alpha-olefins using complex compounds of titanium, nickel and, to a lesser extent, zirconium.

Patent GB 129214 describes a catalytic system that uses a titanium complex. That document also describes a process suitable to produce a catalyst to produce olefins containing 8 to 20 atoms of carbon through ethylene oligomerization.

Patent WO 2005/092821 describes another catalytic oligomerization system. This document presents a process that uses nickel, iron or cobalt catalysts to produce olefins containing from 4 to 12 carbon atoms. However, titanium, nickel and zirconium catalysts often yield products with a wide range of alpha-olefins due to the poor catalytic selectivity to produce olefins through ethylene oligomerization.

The activity and selectivity of catalytic systems are a function of the ligands used, the combination of ligands and the ratio of catalyst/co-catalyst, such as for example $Et_nAlCl_{3-n}$ or methylaluminumoxane.

Among the catalytic systems capable of selective ethylene oligomerization are chromium based catalytic systems.

Chromium catalysts have been widely used in a variety of olefin polymerization processes, such as to produce polyethylene or ethylene and hexene copolymers. Thus such chromium based catalytic systems have been used to selectively produce alpha-olefins. The use of a chromium catalysts with a tridentate ligand containing nitrogen and sulfur atoms as donor ligands for ethylene trimerization is known in the art.

Patent US 2005/131262 describes a highly selective catalytic system used to facilitate the production of 1-hexene in such a way as to avoid the coproduction of significant amounts of polyethylene. Such a catalytic system comprises a combination of multidentate heteroatom ligands useful for catalytic oligomerization of olefins, which ligands include at least three heteroatoms, of which at least one heteroatom is sulfur. Additionally, ligand heteroatoms may be additional atoms of sulfur and at least one atom of nitrogen or phosphorous.

Although alternative catalytic systems for ethylene oligomerization are still widely researched, there is a shortage of more selective, active and higher yield systems for ethylene oligomerization and/or trimerization. This has made it quite attractive to develop catalytic systems with co-catalysts that are more selective for the more desirable alpha-olefin fraction in the range of 6 to 10 carbon atoms.

SUMMARY OF THE INVENTION

The present invention refers to the synthesis of precatalysts and a process for the selective production of alpha-olefins, where the catalysts obtained with such precatalysts are used In oligomerization reactions, in particular ethylene dimerization and trimerization.

More specifically, the present invention refers to the synthesis and use of polydentate coordination compounds of Group 6, such as chromium (III), or Group 10, such as Nickel (II) transition metals.

In other words, the present invention teaches the preparation of Cr based compounds by reacting tridentate nitrogen ligands and a compound equivalent to the $Cr(THF)_3Cl_3$ adduct in a solution of tetrahydrofuran (THF) for 3 hours under an argon atmosphere, and the preparation of Ni based compounds by reaction between the tridentate nitrogen ligands and $NiCl_2 \cdot 6H_2O$ in THF for 24 hours.

In addition, the present invention teaches the preparation of catalytic systems that use catalysts and co-catalysts in olefin oligomerization reactions. Said systems present a high level of catalytic activity and are highly selective for the production of alpha-olefins.

DETAILED DESCRIPTION OF THE INVENTION

The present invention refers to the synthesis of precatalysts. Additionally, the present invention refers to the use of said precatalysts in ethylene oligomerization reactions in a process to selectively produce alpha-olefins.

More specifically, such precursors comprise polydentate coordination compounds comprising compounds based on transition metals in Periodic Table Group 6, particularly chromium (III) and Group 10, particularly nickel (II).

Catalysts for the polymerization of ethylene to produce polyolefins obtained according to the present invention comprise transition metal compound and are represented by the formula $LMX_3$ or $LMX_2$, where: "M" is a transition metal selected from the transition metals in Group 6 or 10 of the Periodic Table of chemical elements, in an oxidation state that may vary from +2 to +6. "X" is an anion; "L" is a ligand according to the structure in Formula 1, also represented by the formula $E[(CH_2)(Pz)]_2R^4$, where: "E" is an atom of oxygen, nitrogen or sulfur bound or not to one or two "Pz" groups and to a radical $R^4$.

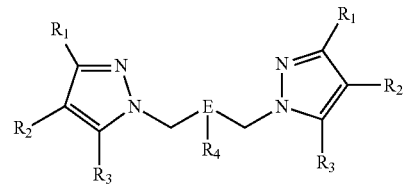

FORMULA 1

Each of the "Pz" groups comprises a pyrazolyl ring with an atom of nitrogen as the heteroatom. For the ligand in the present invention both of the "Pz" groups may be the same or different. Radicals $R^1$, $R^2$ and $R^3$ are atoms of hydrogen or hydrocarbyl radicals located respectively at positions 3, 4 and 5 of the pyrazolyl ring.

According to the present invention, at least one of positions 3, 4 and 5 of the pyrazolyl ring must be filled with a hydrocarbyl radical. The hydrocarbyl radicals may be the same or different. However, if only one or two of these positions are filled with this type of radical, the position that is not filled must contain a hydrogen atom or a hydrocarbyl radical with a number of carbon atoms in the range of $C_1$-$C_3$.

Radicals $R^1$, $R^2$, $R^3$ and $R^4$ may be of the following types: an aliphatic $C_1$-$C_{20}$ hydrocarbyl radical; an aliphatic $C_1$-$C_{20}$ hydrocarbyl radical substituted with at least one $C_6$-$C_{14}$ aromatic radical; a non substituted $C_6$-$C_{20}$ aromatic hydrocarbyl radical; a $C_6$-$C_{20}$ aromatic hydrocarbyl radical substituted with at least one $C_1$-$C_{10}$ alkyl radical.

As illustrative, but not limiting examples of transition metals "M" that may be used in this invention are chromium, molybdenum and tungsten from the Group 6 of the Periodic Table, and nickel and palladium of Group 10 of the Periodic Table.

As illustrative, but not limiting examples of anion "X" that may be used according to this invention are chloride, bromide, fluoride and alkyls such as methyl and ethyl. These ligands may be the same or different.

Illustrative but not limiting examples of substituents $R^1$, $R^2$, $R^3$ located respectively at positions 3, 4 and 5 of the pyrazolyl ring, and $R^4$ are n-butyl, iso-butyl, tert-butyl, iso-pentyl, neo-pentyl, phenyl, benzyl, cumenyl and mesityl.

Optionally the catalytic composition to be used in the oligomerization reaction may comprise one or more types of co-catalyst combined or not with each other, such as an alkylaluminum, hydrocarbylaluminoxane or borane, this last derived from $B(C_6F_5)_3$. Among the examples of preferably used alkylaluminums are trialkylaluminum and the bisalkylaluminum derivatives with $C_1$-$C_8$ alkyl groups, such as for example trimethylaluminum, triisobutylaluminum, dimethylaluminum chloride and diethylaluminum chloride. As examples of preferably used hydrocarbylaluminoxanes are alkylaluminoxanes, arylaluminoxanes and $C_1$-$C_4$ alkyl substituted alkylarylaluminoxanes, such as for example, methylaluminoxane and modified methylaluminoxane. Among the examples of preferably used boranes are $B(C_6F_5)_3$ and its $[(phenyl)_3C][B(C_6F_5)_4]$, $[(methyl)_3HN][B(C_6F_5)_4]$, $[(ethyl)_3HN][B(C_6F_5)_4]$ and $[(phenyl)_3HN][B(C_6F_5)_4]$ derivatives.

When aluminum based co-catalysts are used, co-catalyst and catalyst are used in a molar ratio of between 1:1 and 1:10,000, preferably between 1:50 and 1:5,000 and more preferably between 1:200 and 1:2,000. This molar ratio is defined by the molar ratio between aluminum and Periodic Table Group 4, 5 or 10 metals. When boron based co-catalysts are used the molar ratio is 1:1, defined as the molar ratio between boron and Periodic Table Group 4 or 5 metals.

The catalysts of the present invention may be used in liquid or gas phase oligomerization processes. Such catalysts may participate in the reaction dissolved in the reaction medium, dispersed in an organo-aluminate ionic liquid or in suspension, supported on a suitable medium. Among the suitable supporting media for the present invention are silica, magnesium chloride and alumina. The oligomerization reaction is carried out under the conditions normally used with other types of catalyst. The temperature ranges between −10° C. and 150° C., preferably between 70° C. and 90° C. for Group 6 transition metals and preferably between 20° C. and 60° C. for Group 10 transition metals. Just as with the oligomerization temperature, the pressure and reaction time also depend on the type and condition of the processes and monomers used. The absolute pressure ranges between 1 bar and 140 bar and residence time varies between 1 and 240 minutes. The monomers used in the reaction of the present invention comprise one or more olefins with the number of carbon atoms varying in the range of between 2 and 12 atoms.

The single phase system of the present invention uses non polar or polar compounds as solvents, be they liquid or gas. Examples of these solvents are non-polar alkanes such as hexane, heptane and cyclohexane, or polar alkanes such as toluene, chlorobenze and dichloromethane.

The Cr containing precatalysts employed in the present invention are obtained from the reaction of nitrogen containing tridentate ligands and a compound equivalent to the $Cr(THF)_3Cl_3$ adduct, with a structure represented by Formula 2, in a solvent such as, for example, a tetrahydrofuran (THF) solution under an atmosphere of argon.

FORMULA 2

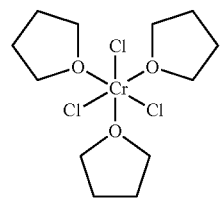

After reaction of such nitrogen containing ligands with the tetrahydrofuran (THF) solution, the THF solvent is evaporated under vacuum yielding the final catalysts: Cr(DMPM-NBz)Cl$_3$ (Formula 3), Cr(DMPMNBu)Cl$_3$ (Formula 4) and Cr(DMPMS)Cl$_3$ (Formula 5).

FORMULA 3

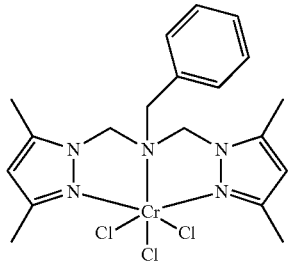

FORMULA 4

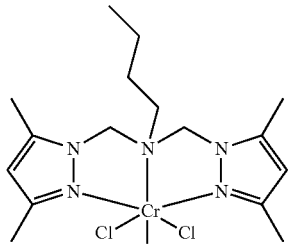

FORMULA 5

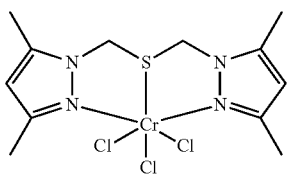

FORMULA 9

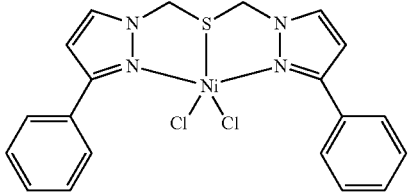

The Ni containing precatalysts employed in the present invention are obtained from the reaction of tridentate nitrogen containing ligands and a compound equivalent to the NiCl$_2$.6H$_2$O adduct in a solvent, such as for example a solution of tetrahydrofuran (THF) under an argon atmosphere.

As examples of tridentate nitrogen ligands we have:

bis[((3,5-dimethyl-1-pyrazolyl)methyl)]benzylamine (DMPMNBz);

bis[((3,5-dimethyl-1-pyrazolyl)methyl)]butylamine (DMPMNBu);

bis[((3,5-dimethyl-1-pyrazolyl)methyl)]sulfide (DMPMS);

bis[((3-phenyl-1-pyrazolyl)methyl)]sulfide (FPMS).

After reaction between such nitrogen ligands and the THF solution the solvent is evaporated under vacuum to yield the final catalysts of the general formula:

Ni(DMPMNBz)Cl$_2$ (Formula 6), Ni(DMPMNBu)Cl$_2$ (Formula 7), Ni(DMPMS)Cl$_2$ (Formula 8) and Ni(FPMS)Cl$_2$ (Formula 9).

FORMULA 6

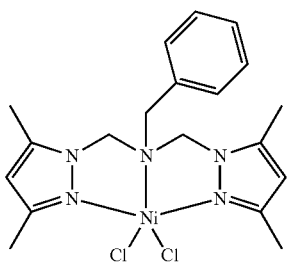

FORMULA 7

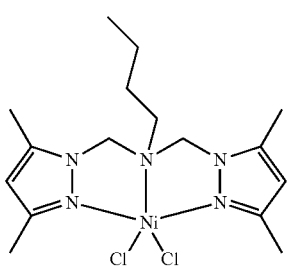

FORMULA 8

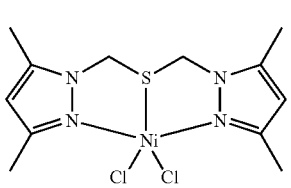

Additionally, the present invention describes catalytic systems that use such catalysts in the presence of a co-catalyst in olefin oligomerization reactions. Such catalytic systems show superior catalytic activity and selectivity for alpha-olefins than those normally found in equivalent traditional systems.

Oligomerization reactions are carried out in a single step in a steel reactor equipped with a mechanical agitator and inlet that enables the continuous injection of ethylene. The reaction temperature is controlled using a thermostatic bath. After this step products are separated and identified.

In the present embodiment of this invention the technique used to identify the products of the ethylene oligomerization reaction was chromatography.

Once the products have been identified by chromatography, the final product is observed to be made up of a variety of olefins of carbon chains containing in the range of 4 to 12 carbon atoms ($C_4$ to $C_{12+}$). However, there is predominance of alpha-olefins as the product of the oligomerization reaction.

A number of adjustments must be made to the reaction system operating conditions, such as changing the ethylene injection pressure, the temperature in the reaction system, the Al/M molar ratio (M=group 6 or 10 transition metal) and the concentration of solvent used so as to increase the yield of the higher value added products or, in other words, products with a longer carbon chain, such as in the range of between 6 and 10 carbon atoms or an even higher content of alpha-olefins.

Below the invention is described in greater detail through examples that must not be interpreted as limiting the scope of the invention.

EXAMPLE 1

Ligand Synthesis

The following ligands were prepared according to methodology known in the art (procedures described in the following articles:

Malachowski, M. G. Davidson *Inorg. Chim. Acta*, 162, (1989), 199 and R. Touzani, A. Ramdani, T. Ben Hadda, S. El Kadiri, O. Maury, H. Le Bozec, P. H. Dixneuf *Synth. Commun.*, 31, (2001), 1315):

bis[((3,5-dimethyl-1-pyrazolyl)methyl)]benzylamine (DMPMNBz);

bis[((3,5-dimethyl-1-pyrazolyl)methyl)]butylamine (DMPMNBu);

Two ligands of the present invention are prepared under an inert argon atmosphere according to the following steps:

(A) Ligand bis[((3,5-dimethyl-1-pyrazolyl)methyl)]sulfide (DMPMS):

1) Reflux a solution of 1-(2-chloromethyl)-3,5-dimethylpyrazole (4.93 g, 34.1 mmol), sodium hydroxide (1.36 g, 34.1 mmol) and Na$_2$S.9H$_2$O (5.13 g, 21.4 mmol) in 50% aqueous ethanol for 3 hours;
2) Cool to ambient temperature;
3) Evaporate under reduced pressure;

4) Add water and extract the product with dichloromethane;
5) Dry over anhydrous Na$_2$SO$_4$;
6) Evaporate to obtain colorless oil.
A 38% yield.
(B) Ligand bis[((3-phenyl-1-pyrazolyl)methyl)]sulfide (FPMS):
1) Keep a mixture of 3-phenylpyrazole (6.34 g, 44 mmol) and paraformaldehyde (1.32 g, 44 mmol) at 120° C. for 48 hours in a Fisher-Porter reactor;
2) Remove the product 1-(hydroxymethyl)-3-phenylpyrazole (0.54 g, 7.0%) from the upper part of the Fischer-Porter reactor wall;
3) Add a solution of thionyl chloride (0.45 mL, 6.2 mmol) in CHCl$_3$ (15 mL) drop wise to a solution of 1-(hydroxymethyl)-3-phenylpyrazole (0.54 g, 3.1 mmol) in CHCl$_3$ (25 mL) at 0° C., then reflux the resulting solution for 4 hours at a 60° C.;
4) Evaporate the solvent and recrystallize from ethanol with a monolayer of ether to obtain an 84% yield of white crystals of 1-(2-chloromethyl)-3,5-dimethylpyrazole;
5) Reflux a solution of 1-(2-chloromethyl)-3,5-dimethylpyrazole (4.93 g, 34.1 mmol), sodium hydroxide (1.36 g, 34.1 mmol) and Na$_2$S.9H$_2$O (5.13 g, 21.4 mmol) in 50% aqueous ethanol for 3 hours;
6) Cool to ambient temperature;
7) Evaporate under reduced pressure;
8) Add water and extract the product with dichloromethane;
9) Dry over anhydrous Na$_2$SO4;
10) Evaporate to obtain a colorless oil.
A 54% yield.

EXAMPLE 2

Synthesis of Catalyst Cr(DMPMNBz)Cl$_3$ (1)

Catalyst Cr(DMPMNBz)Cl$_3$ was synthesized according to the following steps:
1) Prepare a solution of 0.243 g (0.65 mmol) of [Cr(THF)$_3$Cl$_3$] in THF;
2) Add a solution of 0.231 g of DMPMNBz (0.71 mmol) in THF;
3) Stir the resulting mixture on a stirring plate for 3 hours;
4) Evaporate the solvent under vacuum to yield a light green compound Cr(DMPMNBz)Cl$_3$.

The mass of the light green compound Cr(DMPMNBz)Cl$_3$ was 0.270 g, the yield of the Cr(DMPMNBz)Cl$_3$ catalyst synthesis reaction was 87%.

The calculated elemental analysis of C$_{19}$H$_{25}$N$_5$CrCl$_3$ is: C 47.37; H 5.23; N 14.54. Found: C 47.10; H 5.02; N 14.17.

An HRMS-ESI (high-resolution electrospray ionization mass spectrometry) analysis [M-Cl]+ was performed; the calculated mass for C$_{19}$H$_{25}$N$_5$$^{35}$Cl$_2$$^{58}$Cr is 445.08921 and the value found was 445.08805.

EXAMPLE 3

Synthesis of Catalyst Cr(DMPMNBu)Cl$_3$ (2)

Catalyst Cr(DMPMNBu)Cl$_3$ was synthesized according to the following steps:
1) Prepare a solution of 0.299 g (0.80 mmol) of [Cr(THF)$_3$Cl$_3$] in THF;
2) Add a solution of 0.231 g (0.79 mmol) of DMPMNBu in THF;
3) Stir the resulting mixture on a stirring plate for about 3 hours;
4) Evaporate the solvent under vacuum to yield a light green compound, Cr(DMPMNBu)Cl$_3$.

The mass of the green compound Cr(DMPMNBu)Cl$_3$ was 0.243 g and the yield of the reaction to synthesize catalyst Cr(DMPMNBu)Cl$_3$ was 68%.

The calculated elemental analysis of C$_{16}$H$_{27}$N$_5$CrCl$_3$ is: C 42.92; H 6.08; N 15.64. Found: C 42.21; H 5.66; N 15.01.

HRMS-ESI [M-Cl]+ was performed; the calculated mass for C$_{16}$H$_{27}$N$_5$Cl$_2$$^{58}$Cr is 411.10486 and the value found was 411.1050.

EXAMPLE 4

Synthesis of Catalyst Cr(DMPMS)Cl$_3$ (3)

Catalyst Cr(DMPMS)Cl$_3$ was synthesized according to the following steps:
1) Prepare a solution of 0.115 g (0.30 mmol) of [Cr(THF)$_3$Cl$_3$] in THF;
2) Add a solution of 0.085 g (0.34 mmol) of DMPMS in THF;
3) Stir the resulting mixture on a stirring plate for 3 hours;
4) Evaporate the solvent under vacuum to yield a light green compound, Cr(DMPMS)Cl$_3$.

The mass of green compound Cr(DMPMS)Cl$_3$ was 0.243 g and the yield of the catalyst Cr(DMPMS)Cl$_3$ synthesis reaction was 68%

The calculated elemental analysis of C$_{12}$H$_{18}$N$_4$CrCl$_3$S is: C 35.26; H 4.44; N 13.71. Found: C 35.11; H 4.21; N 13.99.

HRMS-ESI [M-Cl]$^+$ analysis was performed, the calculated mass for C$_{12}$H$_{18}$N$_4$$^{35}$Cl$_2$$^{58}$CrS is 406.97229, the mass found was 406.97115.

EXAMPLE 5

Synthesis of Catalyst Ni(DMPMNBz)Cl$_2$ (4)

Catalyst Ni(DMPMNBz)Cl$_2$ was synthesized according to the following steps:
1) Prepare a solution of 0.13 g (0.55 mmol) of NiCl$_2$.6H$_2$O in THF;
2) Add a solution of 0.20 g (0.62 mmol) of DMPMNBz in 10 mL of THF;
3) Stir the resulting mixture on a stirring plate for 24 hours;
4) Evaporate the solvent under vacuum;
5) Wash 3 times with dry ether to yield a green compound Ni(DMPMNBz)Cl$_2$.

The mass of the green compound Ni(DMPMNBz)Cl$_2$ was 0.20 g and the yield of the reaction to synthesize catalyst Ni(DMPMNBz)Cl$_2$ was 75%

The calculated elemental analysis of C$_{19}$H$_{25}$Cl$_2$N$_5$N.2H$_2$O is: C, 46.66; H, 5.98; N, 14.32. Found: C, 46.51; H, 5.90; N, 14.07.

An HRMS-[M-Cl]$^+$ was performed, the calculated mass for C$_{19}$H$_{25}$N$_5$$^{35}$Cl$^{58}$Ni is 416.11520, mass found was 416.1144.

EXAMPLE 6

Synthesis of Catalyst Ni(DMPMNBu)Cl$_2$ (5)

Catalyst Ni(DMPMNBu)Cl$_2$ was synthesized according to the following steps:
1) Prepare a solution of 0.08 g (0.35 mmol) of NiCl$_2$.6H$_2$O in THF;
2) Add a solution of 0.11 g (0.38 mmol) of DMPMNBu in 10 mL of THF;
3) Stir the resulting mixture on a stirring plate for 24 hours;
4) Evaporate the solvent under vacuum;
5) Wash 3 times with dry ether to yield a green compound Ni(DMPMNBu)Cl$_2$.

The mass of green compound Ni(DMPMNBu)Cl$_2$ was 0.12 g and the yield of the catalyst Ni(DMPMNBu)Cl$_2$ synthesis reaction was 91%.

The calculated elemental analysis of C$_{16}$H$_{27}$Cl$_2$N$_5$Ni.2H$_2$O is: C, 42.23; H, 6.87; N, 15.39. Found: C, 42.04; H, 6.64; N, 14.97.

An HRMS-ESI [M-Cl]+ was performed; the calculated mass for C$_{16}$H$_{27}$N$_5$$^{35}$Cl$^{58}$Ni is 382.13085 and the value found was 382.1309.

EXAMPLE 7

Synthesis of Catalyst Ni(DMPMS)C$_{12}$ (6)

Catalyst Ni(DMPMS)Cl$_2$ was synthesized according to the following steps:
1) Prepare a solution of 0.05 g (0.21 mmol) of NiCl$_2$.6H$_2$O in THF;
2) Add a solution of 0.05 g (0.22 mmol) of DMPMS in 10 mL of THF;
3) Stir the resulting solution on a stirring plate for about 24 hours;
4) Evaporate the solvent under vacuum;
5) Wash 3 times with dry ether to yield a green compound Ni(DMPMS)Cl$_2$.

The mass of green compound Ni(DMPMS)Cl$_2$ was 0.14 g and the yield of the catalyst Ni(DMPMS)Cl$_2$ synthesis reaction was 65%.

The calculated elemental analysis of C$_{12}$H$_{18}$Cl$_2$N$_4$NiS.2H$_2$O is: C, 34.65; H, 5.33; N, 13.47. Found: C, 34.51; H, 5.12; N, 13.22.

An HRMS-ESI [M-Cl]+ analysis was performed; the calculated mass for C$_{12}$H$_{18}$N$_4$$^{35}$Cl$^{58}$NiS is 343.02942 and the value found was 343.0291.

EXAMPLE 8

Synthesis of Catalyst Ni(DFPMS)Cl$_2$ (7)

Catalyst Ni(DFPMS)Cl$_2$ was synthesized according to the following steps:
1) Prepare a solution of 0.06 g (0.25 mmol) of NiCl$_2$.6H$_2$O in THF;
2) Add a solution of 0.09 g (0.25 mmol) of DFPMS in 10 mL of THF;
3) Stir the resulting mixture on a stirring plate for 24 hours;
4) Evaporate the solvent under vacuum;
5) Wash 3 times with dry ether to yield a green compound Ni(DFPMS)Cl$_2$.

The mass of green compound Ni(DFPMS)Cl$_2$ was 0.08 g and the yield of the catalyst Ni(DFPMS)Cl$_2$ synthesis reaction was 70%.

The calculated elemental analysis of C$_{20}$H$_{18}$Cl$_2$N$_4$NiS.2H$_2$O is: C, 46.91; H, 4.33; N, 10.94. Found: C, 46.72; H, 4.21; N, 10.72.

An HRMS-ESI [M-Cl]+ analysis was performed; the calculated mass for C$_{20}$H$_{18}$N$_4$$^{35}$Cl$^{58}$NiS is 439.02942 and the value found was 439.0296.

EXAMPLE 9

Chromium Catalyzed Oligomerization Reaction

Alpha-olefins were produced in a moist sterile environment at 80° C. in an autoclave under an atmospheric pressure of 20 atm using a process comprised of the following steps:
1) 40 mL of solution are injected into the reactor under an argon atmosphere (in the present embodiment the solution introduced into the reactor is comprised of a first solution, toluene solution, and a second solution that acts as a co-catalyst, such as for example a solution of methylaluminoxane, MAO, at a molar Al/Cr ratio equal to 300, (mol/mol);
2) The oligomerization reaction system is saturated with ethylene;
3) The oligomerization reaction is initiated by adding to the reactor system 30 μmol of precatalyst Cr(DMPMNBz)Cl$_3$ diluted in toluene;
4) The oligomerization reaction is quenched by venting and cooling the system.

Initially the ethylene solution is injected into the reaction system continuously to maintain a constant pressure of ethylene. About 15 minutes into the oligomerization reaction the reaction is quenched by venting and cooling the system to −20° C. An amount of cyclohexane is then added to the system. The cyclohexane solution serves as an internal standard for the reaction and the amount added must respect the mixture's proportions. After adding the cyclohexane solution the product of the oligomerization reaction with is analyzed by gas chromatography.

The product of the oligomerization reaction with precursor Cr(DMPMNBz)Cl$_3$ obtained as described in example 2 is a mixture of olefins, predominantly alpha-olefins, with an even number of carbon atoms, preferably olefins with between 4 and 12 carbon atoms.

The characteristics of the oligomers obtain thusly are shown in Table 1.

EXAMPLE 10

Chromium Catalyzed Oligomerization Reaction

The oligomerization reaction was performed as described in Example 9 except for the temperature, which was maintained at 100° C. The product of the oligomerization reaction with precursor Cr(DMPMNBz)Cl$_3$ is a mixture of olefins, predominantly alpha-olefins with an even number of carbons, preferably olefins with about 4 to 12 carbon atoms.

The characteristics of the oligomers obtain thusly are described in Table 1.

EXAMPLE 11

Chromium Catalyzed Oligomerization Reaction

The oligomerization reaction was saturated with precatalyst Cr(DMPMNBu)Cl$_3$ obtained as described in Example 3, [and] with a solution of ethylene, the oligomerization reaction was initiated by adding 30 mmol of precatalyst Cr(DMPMNBu)Cl$_3$ diluted in toluene to the reaction system.

The oligomerization reaction proceeds analogously to Example 9, except for the precatalyst.

The product of the oligomerization reaction with precursor Cr(DMPMNBu)Cl$_3$ is a mixture of olefins, predominantly alpha-olefins with an even number of carbons, preferably olefins with 4 to 12 carbon atoms.

The characteristics of the oligomers obtain thusly are described in Table 1.

EXAMPLE 12

Chromium Catalyzed Oligomerization Reaction

The oligomerization reaction was saturated with precatalyst Cr(DMPMS)Cl$_3$ obtained as described in Example 4, [and] with a solution of ethylene, the oligomerization reaction was initiated by adding 30 μmol of precatalyst Cr(DMPMS)Cl$_3$ diluted in toluene to the reaction system.

The oligomerization reaction proceeded analogously to Example 9 except for the precatalyst.

The product of the oligomerization reaction with precursor Cr(DMPMS)Cl$_3$ is a mixture of olefins, predominantly alpha-olefins with an even number of carbons, preferably olefins with 4 to 12 carbon atoms.

The characteristics of the oligomers obtain thusly are described in Table 1.

EXAMPLE 13

Chromium Catalyzed Oligomerization Reaction

The oligomerization reaction proceeded analogously to Example 12 except that the amount of precatalyst used was 10 µmol.

The product of the oligomerization reaction with precursor Cr(DMPMS)Cl$_3$ is a mixture of olefins, predominantly alpha-olefins with an even number of carbons, preferably olefins with 4 to 12 carbon atoms.

The characteristics of the oligomers obtain thusly are described in Table 1.

EXAMPLE 14

Nickel Catalyzed Oligomerization Reaction

Alpha-olefins were produced in a moist sterile environment using an autoclave at a temperature in the range of 30° C. and 60° C. and an atmospheric pressure of 20 atm, using a process comprised of the following steps:
1) 40 mL of a solution are injected into the reactor under an argon atmosphere (in the present embodiment the solution introduced to the reactor comprises a first, toluene solution, and a second solution that serves as a co-catalyst, such as for example a solution of methylaluminoxane, MAO, at a molar Al/Cr ratio equal to 250 mol/mol);
2) The oligomerization reaction system is saturated with ethylene;
3) The oligomerization reaction is initiated by adding to the reactor system 10 µmol of precatalyst Ni(DMPMNBz)Cl$_2$ diluted in toluene;
4) The oligomerization reaction is quenched by venting and cooling the system.

Initially the ethylene solution is injected into the reaction system continuously to maintain a constant pressure of ethylene. About 20 minutes into the oligomerization reaction the reaction is quenched by venting and cooling the system to −20° C. An amount of cyclohexane is then added to such system. Such cyclohexane solution serves as an internal standard for the reaction and the amount added must respect the mixture's proportions. After addition of the cyclohexane solution the product of the oligomerization reaction is analyzed using gas chromatography.

The product of the oligomerization reaction with precursor Ni(DMPMNBz)Cl$_2$ obtained as described in Example 5 is a mixture of butenes, predominantly 1-butene, with a small fraction analyzed as 1-hexene.

The characteristics of the oligomers obtained in these reactions are shown in Table 2.

EXAMPLE 15

Nickel Catalyzed Oligomerization Reaction

The oligomerization reaction proceeded analogously to Example 14 except for the temperature, which was maintained at 60° C.

The product of the oligomerization reaction with precursor Ni(DMPMNBz)Cl$_2$ is characterized as a mixture of butenes, predominantly 1-butene, with a small fraction analyzed as 1-hexene.

The characteristics of the oligomers obtained in these reactions are shown in Table 2.

EXAMPLE 16

Nickel Catalyzed Oligomerization Reaction

The oligomerization reaction was carried out as described in example 14, except for the precatalyst.

The product of the oligomerization reactions with precursor Ni(DMPMNBu)Cl$_2$ obtained as described in Example 6 is characterized by a mixture of butenes, predominantly 1-butene, with a small fraction analyzed as 1-hexene.

The characteristics of the oligomers obtained in these reactions are shown in Table 2.

EXAMPLE 17

Nickel Catalyzed Oligomerization Reaction

The oligomerization reaction was saturated with precatalyst Ni(DMPMS)Cl$_2$, obtained as described in Example 7, [and] with an ethylene solution and the oligomerization reaction initiated by adding 10 µmol of precatalyst Ni(DMPMS)Cl$_2$ diluted in toluene to the reaction system.

The oligomerization reaction proceeded analogously to Example 14 except for the precatalyst.

The product of the oligomerization reaction with precursor Ni(DMPMS)Cl$_2$ is characterized by a mixture of butenes, predominantly 1-butene.

The characteristics of the oligomers obtain thusly are described in Table 2.

EXAMPLE 18

Nickel Catalyzed Oligomerization Reaction

The oligomerization reaction system was saturated with precatalyst Ni(DFPMS)Cl$_2$ obtained as described in Example 8, [and] with a solution of ethylene and the oligomerization reaction initiated by adding to the system 10 µmol of precatalyst Ni(DFPMS)Cl$_2$ diluted in toluene.

The oligomerization reaction was carried out as described in example 14 except for the type of precatalyst.

The product of the oligomerization reaction with precursor Ni(DFPMS)Cl$_2$ is characterized by a mixture of butenes, predominantly 1-butene with a small fraction analyzed as 1-hexene.

The characteristics of the oligomers obtain thusly are described in Table 2.

EXAMPLE 19

Nickel Catalyzed Oligomerization Reaction

The oligomerization reaction was carried out as described in example 14 except for the type of co-catalyst. Instead of MAO, diethylaluminum chloride (DEAC) was used (Al/Ni=250).

The product of the oligomerization reaction with precursor Ni(DMPMNBz)Cl$_2$ is characterized by a mixture of butenes, predominantly 1-butene.

The characteristics of the oligomers obtain thusly are described in Table 2.

EXAMPLE 20

Nickel Catalyzed Oligomerization Reaction

The oligomerization reaction proceeded analogously to Example 16 except for the type of co-catalyst used. Diethylaluminum chloride (DEAC) was used (Al/Ni=250).

The product of the oligomerization reaction with precursor Ni(DMPMNBu)Cl$_2$ is characterized as a mixture of butenes, predominantly 1-butene, with a small fraction analyzed as 1-hexene.

The characteristics of the oligomers obtained in these reactions are shown in Table 2.

EXAMPLE 21

Nickel Catalyzed Oligomerization Reaction

The oligomerization reaction was carried out as described in example 17, except for the type of co-catalyst. Diethylaluminum chloride (DEAC) was used (Al/Ni=250).

The product of the oligomerization reaction with precursor Ni(DMPMS)Cl$_2$ is characterized by a mixture of butenes, predominantly 1-butene, with a small fraction analyzed as 1-hexene.

The characteristics of the oligomers obtain thusly are described in Table 2.

EXAMPLE 22

Nickel Catalyzed Oligomerization Reaction

The oligomerization reaction proceeded analogously to Example 21, except for the molar ratio (Al/Ni=50).

The product of the oligomerization reaction with precursor Ni(DMPMS)Cl$_2$ is characterized by a mixture of butenes, predominantly 1-butene, with a small fraction analyzed as 1-hexene.

The characteristics of the oligomers obtain thusly are described in Table 2.

EXAMPLE 23

Nickel Catalyzed Oligomerization Reaction

The oligomerization reaction proceeded analogously to Example 18 except for the type of co-catalyst used. Diethylaluminum chloride (DEAC) was used (Al/Ni=250).

The product of the oligomerization reaction with precursor Ni(DFPMS)Cl$_2$ is characterized by a mixture of butenes, predominantly 1-butene, with a small fraction analyzed as 1-hexene.

The characteristics of the oligomers obtain thusly are described in Table 2.

The foregoing descriptions of specific embodiments of the present invention have been described for the purposes of illustration and description. While certain embodiments have been described and exemplified above, various other embodiments will be apparent to those skilled in the art from the foregoing disclosure. The present disclosure is not limited to the particular embodiments described and exemplified, and the embodiments are capable of considerable variation and modification without departure from the scope of the appended claims.

The result of the oligomerization reaction using a Cr (III) catalyst containing ligand bis[(3,5-dimethyl-1-pyrazolyl) methyl)]benzylamine (DMPMNBz) (Example 9) demonstrates that this catalytic system is highly selective for producing 1-hexene ($\alpha$-C$_6$=39.34%) and 1-octene ($\alpha$-C$_8$=23.54%).

The selectivity of this system remains high for 1-hexene production ($\alpha$-C$_6$=29.59%) and 1-octene ($\alpha$-C$_8$=19.98%) even when using a higher reaction temperature (Example 10, 100° C.).

Replacement of the benzyl (Bz) group with an n-butyl (Bu) group (Example 11) shows that the Cr (III) continues to exhibit high selectivity for the production of 1-hexene ($\alpha$-C$_6$=24.54%) and 1-octene ($\alpha$-C$_8$=14.69%). These results indicate that the formation of five-member ring systems produces catalysts that are more selective for 1-hexene and 1-octene.

The oligomerization reaction using Cr(DMPMS)Cl$_3$ (Example 12) shows that this catalyst has a high turnover frequency, on the order of 26.326 h−1, and is highly selective for alpha-olefins (>91.0%).

Studies related to the influence of catalyst concentration in the reactor show that reducing the concentration of catalyst from 30 to 10 µmol (Example 13) resulted in an increase in the "TOF" of from 26.326 h−1 to 45.741 h−1, suggesting that the use of a smaller amount of catalyst determines an increase in the formation of catalytically active species.

MAO activated Ni(II) catalysts are active for ethylene dimerization. Moderate turnover frequencies were obtained (TOFs) of between 3,900 and 18,900 h$^{-1}$ (Examples 14, 16 and 18).

The catalytic system containing a ligand with a sulfur bridge and substituted methyls in positions 3 and 5 of the pyrazole rings resulted in a high "TOF" of 104,500 h$^{-1}$ (Example 17).

Catalytic performance for the dimerization of ethylene is substantially influenced by the type of ligand. Thus the catalyst containing N-benzyl (Example 14) as a substituent is 3 times more active than the catalyst containing N-butyl (Example 16). However, in the last case the selectivity for 1-butene was best, reaching 93.7% with only minimal production of 2-butenes and hexene.

Also, the presence of bulkier groups such as phenyl (compared to methyl groups) on the pyrazolyl groups causes a significant decrease in catalytic activity of the (NSN)Ni(II) systems (compare Examples 17 and 18).

Additionally, systems with catalysts containing bis(pyrazolyl) ligands with sulfur bridges (Example, 17, TOF=104,500 h$^{-1}$), such as ligand NiCl$_2$\{bis[2-((3,5-dimethl-1-pyrazolyl)methyl)]sulfide\}, which had almost twice the catalytic activity of ligand NiCl2\{bis[2-((3,5-dimethyl-1-pyrazolyl)ethyl)]sulfide\} (TOF—57,200 h$^{-1}$, Ajellal, N.; Kuhn, M. C. A.; Boff, A. D. G.; Hoerner, M.; Thomas, C. M.; Carpentier, J.-F.; Casagrande Jr., O. L.; *Organometallics*, 2006, 25, 1213), show that the formation of a five-member ring system gives the system enhanced stability. Additionally, no significant impact on the selectivity of 1-butene was observed, which remained around 70%-73%.

For all MAO activated nickel complexes the butene selectivity is high, especially for 1-butene, reaching 81.1%-93.7% of the total olefins produced in the oligomerization reaction under these conditions.

Larger amounts of 2-butene (about 26%) are produced with a Ni(II) catalyst containing a sulfur bridge (Example 17). In all cases only minimal amounts of hexene were produced and no polymer was detected.

TABLE 1

Gas chromatography analyses: product distribution for Cr (III) catalyzed oligomerization reactions

| EXAMPLE | % $C_4$ (a - $C_4$) | % $C_6$ (a - $C_6$) | % $C_8$ (a - $C_8$) | % $C_{10}$ (a - $C_{10}$) | % $C_{12+}$ | Oligomer (mg) | TOF (c) ($h^{-1}$) |
|---|---|---|---|---|---|---|---|
| EXAMPLE 9 | 7.90 (51.19) | 42.20 (93.24) | 33.07 (71.19) | 6.09 (89.61) | 10.7 | 342 | 1,527 |
| EXAMPLE 10 (a) | 15.58 (50.14) | 32.67 (90.59) | 32.01 (62.42) | 10.18 (9.57) | 9.57 | 324 | 1,547 |
| EXAMPLE 11 | 14.74 (87.6) | 26.17 (93.8) | 16.33 (90.0) | 12.41 (92.6) | 30.35 | 1,117 | 4,967 |
| EXAMPLE 12 | 16.79 (90.47) | 18.80 (93.74) | 19.24 (87.26) | 14.89 (88.68) | 30.28 | 4,966 | 26,326 |
| EXAMPLE 13 (b) | 11.19 (91.97) | 14.23 (95.78) | 18.57 (83.07) | 15.51 (96.35) | 40.50 | 3,298 | 45,741 |

Reaction conditions: 80° C., 20 bar, 50 mL toluene, 30 μmol Cr, Al/Cr = 300 (MAO).
(a) 100° C., 20 bar, 50 mL toluene, 30 μmol Cr, Al/Cr = 300 (MAO).
(b) 800° C., 20 bar, 50 mL toluene, 10 μmol Cr, Al/Cr = 300 (MAO).
(c) Moles of ethylene converted (moles Cr)$^{-1}$ h$^{-1}$ determined by quantitative gas liquid chromatography, Cn, quantity of olefins with carbon atoms in the oligomers; α - Cn, quantity terminal alkenes in the Cn fraction; determined by quantitative GLC.

TABLE 2

Gas chromatography analyses: total $C_4$ and isomer distribution from the Ni (II) catalyzed oligomerization reactions

| Catalyst | Co-catalyst | % $C_4$ total | % α-$C_4$ | % $C_4$ (cis) | % $C_4$ (trans) | % α-$C_6$ | Oligomer (mg) | TOF (c) ($h^{-1}$) |
|---|---|---|---|---|---|---|---|---|
| EXAMPLE 14 | MAO | 96.3 | 84.4 | 8.5 | 6.5 | 3.7 | 1054 | 11,300 |
| EXAMPLE 15 (a) | MAO | 95.3 | 82.3 | 14.4 | 2.5 | 4.7 | 172 | 1,700 |
| EXAMPLE 16 | MAO | 100 | 93.7 | 5.1 | 1.3 | — | 371 | 3,900 |
| EXAMPLE 17 | MAO | 97.8 | 71.9 | 16.9 | 9.0 | 2.2 | 9,761 | 104,500 |
| EXAMPLE 18 | MAO | 98.0 | 81.8 | 11.7 | 6.1 | 1.9 | 1,782 | 18,900 |
| EXAMPLE 19 | DEAC | 100 | 81.3 | 10.6 | 8.1 | — | 6,470 | 69,800 |
| EXAMPLE 20 | DEAC | 98.4 | 72.0 | 15.0 | 11.5 | 1.6 | 8,389 | 89,600 |
| EXAMPLE 21 | DEAC | 98.2 | 72.5 | 14.7 | 11.0 | 1.7 | 8,499 | 91,000 |
| EXAMPLE 22 (b) | DEAC | 98.3 | 76.3 | 12.9 | 9.1 | 1.7 | 7,380 | 79,000 |
| EXAMPLE 23 | DEAC | 98.0 | 77.6 | 12.8 | 9.1 | 1.9 | 3,192 | 33,900 |

Reaction conditions: 30° C., 20 bar, 40 mL toluene, 10 μmol Cr Al/Ni = 250.
(a) 60° C., 20 bar, 40 mL toluene, 10 μmol Cr, Al/Ni = 250 (MAO).
(b) 30° C., 20 bar, 40 mL toluene, 10 μmol Cr, Al/Ni = 50 (MAO).
(c) Moles ethylene converted (moles Ni)$^{-1}$ $^{h-1}$ determined by quantitative gas liquid chromatography (GLC), $C_n$, quantity of olefins with carbon atoms in the oligomers; α-$C_n$, quantity of terminal alkenes in the $C_n$ fraction determined by quantitative GLC.

The invention claimed is:

1. A catalyst of the general formula LMX$_n$, where "M" is a metal, "X" is an anion, and "n" is the number of anions "X" present in each molecule, varying from 1 to 3, and "L" is a polydentate nitrogen ligand of formula:

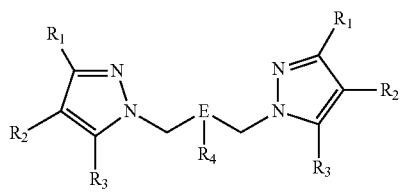

wherein "E" is a heterocycle pyridine ring, an imidazole ring or an element selected from among oxygen or sulfur, $R_1$, $R_2$ and $R_3$ are each, independently of one another, located respectively at positions 3, 4 and 5 of the pyrazolyl radical and selected from among hydrogen atoms, hydrocarbyl radicals with a number of carbon atoms equal to or greater than 1, wherein when E is a heterocycle pyridine ring or an imidazole ring, $R_4$ is an atom of hydrogen or a radical selected from among aliphatic $C_4$-$C_{20}$ hydrocarbyls, an aliphatic $C_1$-$C_{20}$ hydrocarbyl containing at least one $C_6$-$C_{14}$ aromatic radical, an non substituted $C_6$-$C_{20}$ aromatic radical and a $C_6$-$C_{20}$ aromatic hydrocarbyl with at least one $C_1$-$C_{10}$ alkyl substituent, wherein when E is oxygen or sulfur, $R_4$ is absent, and
wherein when E is a heterocycle pyridine ring, $R_4$ is not hydrogen.

2. The catalyst according to claim 1, wherein at least one of the positions 3, 4 or 5 of the pyrazolyl ring is occupied by a hydrocarbyl radical.

3. The catalyst according to claim 1, wherein said $R_1$ radical located at position 3 of the pyrazolyl ring is selected from among n-butyl, isobutyl, tert-butyl, iso-pentyl, neo-pentyl, phenyl, benzyl, cumenyl or mesityl.

4. The catalyst according to claim 1 wherein said anions "X" is selected from the group consisting of chloride, bromide, fluoride or alkyl.

5. The catalyst according to claim 1, wherein said transition metal "M" is selected from elements of Periodic Table Groups 6 and 10.

6. The catalyst according to claim 1, wherein n is equal to 3, and the catalyst is obtained by a reaction between tridentate nitrogen ligands and a Cr(THF)$_3$Cl$_3$ adduct or an equivalent compound in the presence of a solvent.

7. The catalyst according to claim 1, wherein n is 2, wherein the catalyst is obtained by a reaction in the presence of a solvent, between tridentate nitrogen ligands and a Ni(dimethoxyethane)Cl$_2$ adduct or equivalent compound, or a nickel salt of general formula NiX$_2$, and wherein "X" is selected from the group consisting of a halogen, acetate, acetylketonate or nitrate.

8. The catalyst according to claim 1, wherein said catalyst is Cr(DMPMS)Cl$_3$ (Formula 5), with the following structural formula:

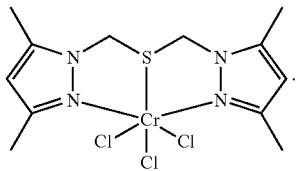

FORMULA 5

9. A process for obtaining alpha-olefins by oligomerization of one or more olefins, catalyzed by polydentate coordination compounds comprised of compounds based on Periodic Table Group 6 transition metals and/or compounds based on group 10 transition metals, at temperatures ranging from between 70° C. and 90° C. for Group 6 transition metals, and at temperatures between 20° C. and 60° C. for Group 10 transition metals, and an absolute pressure varying in the range from between 1 bar and 140 bar, and a residence time varying in the range from between 1 and 240 minutes, characterized by using a catalytic system comprised of:

a catalyst obtained from the reaction of a precursor containing a tridentate ligand group and a transition metal salt selected from among Periodic Table Groups 6 and 10;

an alkylaluminum, hydrocarbylaluminoxane or borane type catalyst derived from B(C$_6$F$_5$)$_3$, either alone or in combination, and comprising the following steps:

1) prepare the catalyst of the general formula LMX$_n$ according to claim 1, prepare a reaction mixture containing said catalyst, a solvent and an olefin;

provide conditions such that this reaction mixture will react in solution to yield a series of alpha-olefins; and separate the alpha-olefins in the end product, comprised of a mixture of olefins with carbon chains in the range of 4 to 12 carbon atoms.

10. The process to obtain alpha-olefins according to claim 9, characterized by a molar ratio between the boron in the borane type co-catalyst and the Group 6 metal "M" in the catalyst being equal to 1:1.

11. The process to obtain alpha-olefins according to claim 9, characterized by a molar ratio between the aluminum in the organoaluminum co-catalyst and Group 6 and 10 metal "M" in the catalyst of between 1:1 and 1:10,000.

12. The process to obtain alpha-olefins according to claim 9, characterized by said organoaluminum co-catalyst being a hydrocarbylaluminoxane selected from among alkylaluminoxanes, arylaluminoxanes and alkylarylaluminumoxanes with C$_1$-C$_4$ alkyl groups.

13. The process to obtain alpha-olefins according to claim 9 characterized by said organoaluminum co-catalyst being a mixture containing at least two alkylaluminum or hydrocarbylaluminoxane compounds.

14. The process to obtain alpha-olefins according to claim 9, characterized by the use of a precatalyst selected from the group consisting of Cr(DMPMS)Cl$_3$ (Formula 5), Ni(DMPMS)Cl$_2$ (Formula 8) and Ni(DFPMS)Cl$_2$ (Formula 9) in liquid or gas phase.

15. The process to obtain alpha-olefins according to claim 9, characterized by said catalysts participating in the reaction, both solubilized in the reaction medium as well as dispersed in an organoaluminate ionic liquid or in suspension, supported on silica, magnesium chloride or alumina.

16. The process to obtain alpha-olefins according to claim 9, characterized by the monomers used in the reaction being comprised of one or more olefins with 2 to 12 carbon atoms.

17. The process to obtain alpha-olefins according to claim 16, characterized by the olefin fraction present in the reaction mixture in the largest amount containing ethylene or propene.

18. The process to obtain alpha-olefins according to claim 15, characterized by the reaction being conducted in a single-phase system in a non-polar or polar liquid or gas solvent.

19. The process to obtain alpha-olefins according to claim 18, characterized by the non-polar solvent being selected from among hexane, heptane or cyclohexane, and the polar solvent being selected from among toluene, chlorobenzene or dichloromethane.

20. The catalyst according to claim 5, wherein the metal "M" is selected from elements of Group 6 of the Periodic table, in oxidation states of between +2 and +6, chosen between chromium, molybdenum or tungsten.

21. The catalyst according to claim 5, wherein the metal "M" is selected from elements of Group 10 of the Periodic table, in oxidation states of between +2 and +6, chosen between nickel or palladium.

* * * * *